United States Patent [19]

Demus et al.

[11] Patent Number: 4,615,824

[45] Date of Patent: Oct. 7, 1986

[54] MIXING COMPONENT FOR LIQUID CRYSTAL SUBSTANCES

[75] Inventors: Dietrich Demus; Horst Zaschke, both of Halle; Gerhard Pelzl, Halle-Neustadt; Carsten Tschierske, Halle, all of German Democratic Rep.

[73] Assignee: VEB Werk fuer Fernsehelektronik im VEB Kombinat Mikroelektronik, Berlin, German Democratic Rep.

[21] Appl. No.: 675,672

[22] Filed: Nov. 28, 1984

[30] Foreign Application Priority Data

Dec. 22, 1983 [DD] German Democratic Rep. .................................. 2583833

[51] Int. Cl.$^4$ ............ C09K 3/34; C09K 19/52; G02F 1/13; C07F 9/15
[52] U.S. Cl. ............................ 252/299.5; 252/299.61; 558/74; 350/350 R; 544/243; 544/333; 544/335; 549/221
[58] Field of Search ............ 252/299.5, 299.61; 350/350 R; 260/934, 936, 937; 544/243, 333, 335; 549/221

[56] References Cited

U.S. PATENT DOCUMENTS

| | | | |
|---|---|---|---|
| 4,122,026 | 10/1978 | Osman ........................... | 252/299.5 |
| 4,293,698 | 10/1981 | Toriyama et al. ............ | 252/299.61 |
| 4,311,610 | 1/1982 | Zaschke et al. ............... | 252/299.61 |
| 4,344,856 | 8/1982 | Demus et al. ................. | 252/299.61 |
| 4,348,324 | 9/1982 | Demus et al. ................. | 252/299.61 |
| 4,356,104 | 10/1982 | Hsu ................................ | 252/299.61 |
| 4,358,393 | 11/1982 | Zaschke et al. ............... | 252/255.61 |
| 4,537,698 | 8/1985 | Sucrow et al. ................ | 252/299.61 |

FOREIGN PATENT DOCUMENTS

| | | | |
|---|---|---|---|
| 2835492 | 2/1980 | Fed. Rep. of Germany ..................... | 252/299.61 |
| 58-136680 | 8/1983 | Japan ............................ | 252/299.5 |
| 59-70684 | 4/1984 | Japan ............................ | 252/299.5 |
| 2092169 | 8/1982 | United Kingdom .......... | 252/299.63 |

OTHER PUBLICATIONS

Karamysheva, L. A., et al., Advances in Liquid Crystal Research & Applications, Bata, L. Ed., Pergamon Press, Oxford, pp. 997–1002 (1980).
Zaschke, H., Advances in Liquid Crystal Research & Applications, Bata, L. Ed., Pergamon Press, Oxford, pp. 1059–1074 (1980).
C.A., vol. 97, 55893.
C.A., vol. 94, 173786.
C.A., vol. 94, 156876.
C.A., vol. 89, 191878.

Wadsworth, Jr., W. S., et al., JACS, vol. 84, No. 4, pp. 610–617 (1962).

Primary Examiner—Teddy S. Gron
Attorney, Agent, or Firm—Jordan and Hamburg

[57] ABSTRACT

A mixing component for nematic liquid-crystalline substances used in optoelectronic components for the rendition of numbers, symbols and images. The object of the invention is to reduce, in components for nematic liquid crystal substances, the threshold and operating voltages. It has been found, that the addition of one or more 1-oxa-2,6,7-trioxane-1-phospha-bicyclo-derivatives having the general formula

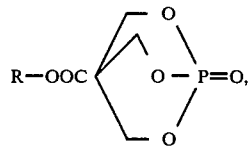

wherein

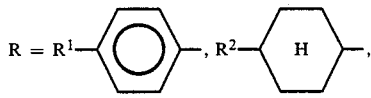

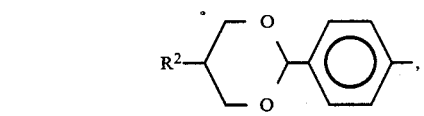

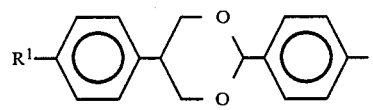

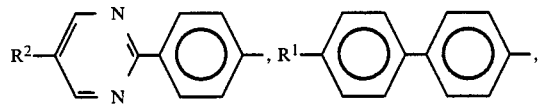

with $R^1 = C_nH_{2n+1}-$, $C_nH_{2n+1}O-$, $C_nH_{2n+1}COO-$, $C_nH_{2n+1}OCOO-$, $R^2 + C_nH_{2n=1}-$
with n=an integer from 1 to 10
to nematic liquid crystal substances, considerably reduces the operating voltage.

11 Claims, No Drawings

MIXING COMPONENT FOR LIQUID CRYSTAL SUBSTANCES

BACKGROUND OF THE INVENTION AND PRIOR ART STATEMENT

The invention relates to a mixing component of liquid crystal substances for the use in optoelectronic components for the rendition of numbers, symbols and images.

Nematic liquid crystals can be used in optoelectronic components (displays) for the modulation of passing through or reflected light, as well as for the rendition of numbers, symbols and images, see H. Kelker, R. Hatz, Handbook of Liquid Crystals, Publisher Chemie Seinheim, 1980.

Technically mostly mixtures of strongly positive dielectric anisotropy are required, which are also used in displays on the basis of the Schadt-Helfrich-effect (TNP-cells). The effect occurs only above a threshold voltage $U_o$, of the following formula:

$$U_o = \pi \left( \frac{K_{ii}}{\epsilon_o \Delta \epsilon} \right)^{\frac{1}{2}}$$

$K_{ii}$ = effective elastic constant
$\epsilon_o$ = influence constant
$\Delta \epsilon$ = dielectric anisotropy The operating voltage, at which the displays have to be operated, lies higher than $U_o$. It holds true, however, that the lower $U_o$ is, the lower is the operating voltage. By the optimization of liquid crystal mixtures for practical use, furthermore, many various parameters have to be taken into consideration, among others melting and clarification temperature, melting enthalpy, viscosity, optic and dielectric anisotropy, elastic constant. Frequently, a mixture meets the requirements in several characteristics, however, the dielectric anisotropy is too low, and consequently the threshold and operating voltage is too high.

SUMMARY OF THE INVENTION

The object of the invention consists of a mixing component for nematic liquid crystal substances which lowers the threshold and operating voltage.

An object is to reduce, in components for nematic liquid crystal substances, the threshold and operating voltages.

Another object of the invention is the use of substances, which strongly increase the dielectric anisotropy in mixtures.

These and other objects and advantages of the present invention will become evident from the description which follows.

It has been found that by the addition of one or more 1-oxa-2,6,7-trioxa-1-phospha-bicyclo[2.2.2]octane-derivatives having the general formula

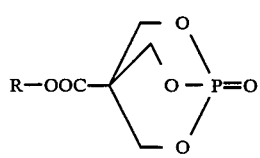

wherein

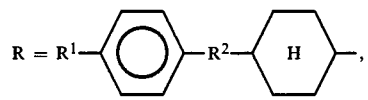

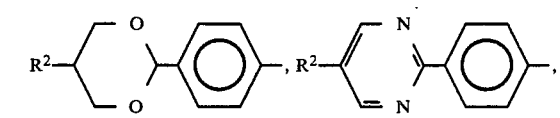

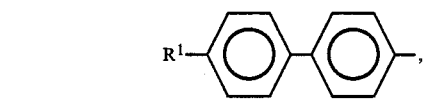

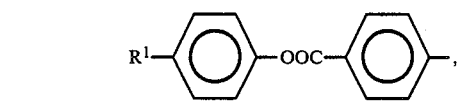

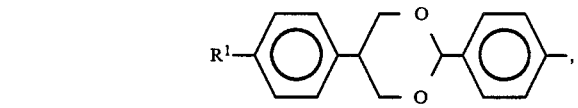

with $R^1 = C_nH_{2n+1}-$, $C_nH_{2n+1}O-$, $C_nH_{2n+1}COO-$, $C_nH_{2n+1}OCOO-$ $R^2 = C_nH_{2n+1}-$ with n an integer from 1 to 10.

to nematic liquid crystal mixtures, the dielectric anisotropy is strongly increased, and as a result the operating voltage is decreased.

DETAILED DESCRIPTION OF THE PREFERRED EMBODIMENTS

The production of the new substances according to the invention proceeds according to the following schematic representation:

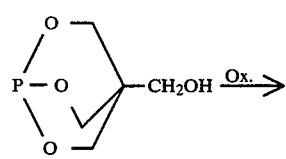

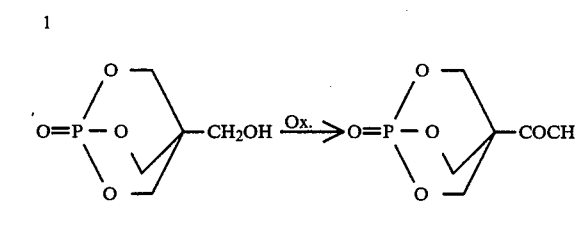

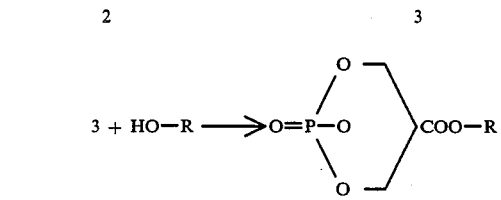

By reesterification of triethylphosphite with pentaerythrite and oxidation of the resulting 4-hydroxymethyl-1-2,6,7-trioxa-1-phosphabicyclo[2.2.2]octane 1 with a solution of 30% of $H_2O_2$ in isopropanol, according to W. S. Wadworth, W. P. Emmons, J. Amer. Chem. Soc. 84, 610 (1962), 2 is attainable in good yields. The oxidation of 2 to 3 succeeds only with $KMnO_4$ in a pyridine water-mixture of a yield of 45%. The esterification of 3 with substituted phenols or trans-4-alkylcyclohexanols to 4 can be performed according to the Einhorn-variant, as well as by means of dicyclohexylcarbodiimide.

EXAMPLE 1

Production of 1-oxa-2,6,7-trioxa-1-phosphabicyclo[2.2.2]octane-4-carboxylic acid ester 4

1.
1-oxa-2,6,7-trioxa-1-phosphabicyclo[2.2.2]octane-4-carboxylic acid 3

To this solution of 18 g (0.1 mol) 2 in 100 ml pyridine is added a solution of 25 g (0.16 mol) $KMnO_4$ in 400 ml pyridine and 100 ml water and stirred at room temperature until decolorization (5 to 6 days). The precipitated $MnO_2$ is suctioned off and the mother liquor is reduced in vacuum at 40° C. The residue is dissolved in 150 ml $H_2O$, shaken out twice with ether, and then the aqueous phase is acidified with 11 ml concentrated HCl at 20° C. After cooling to 15° C., the fallen out precipitation is suctioned off, washed three times with 20 ml icewater, as well as once with ice-cold ethanol, and dried in air. 3 can be used without further purification for esterification.

Yield: 8.2 g (45% of the theoretical amount) F.P: above 260° C. decomposition

2.
1-oxa-2,6,7-trioxa-1-phosphabicyclo[2.2.2]octane-4-carboxylic acid ester 4 (see. Table 1)

To a suspension of 0.8 g (0.04 mol) 3 in 10 ml abs. pyridine under stirring at 0° C. are added dropwise 1 ml thionylchloride and stirred at room temperature for 30 minutes. Then the solution of 0.05 ml of the corresponding phenol in 5 ml abs. pyridine is added and stirred at room temperature for 24 hours. Subsequently, all volatile products are distilled off at 40° C. in vacuum, the residue is mixed with diluted HCl, stirred for 15 minutes, the precipitate suctioned off, washed with water and ether several times, and dried in air. 4 are recrystallized from ethanol. The yields amount to 50 to 60% of the theoretical amount. 4f and 4g can be synthesized under addition of an acylation catalyst, for instance, 4-dimethylaminopyridine.

EXAMPLE 2

The effect of the substances 4b, 4c and 4e according to the invention, will be demonstrated on the following mixtures:

| Basic mixture | | | | Component |
|---|---|---|---|---|
| $C_4H_9$—⟨H⟩—COO—⟨◯⟩—$OC_2H_5$ | | | | A |
| $C_4H_9$—⟨H⟩—COO—⟨◯⟩—$OC_6H_{13}$ | | | | B |
| | | 5 4e | 5 4b | 5 4c |
| Composition mol-% | 38 A 62 B | 50 A 45 B | 50 A 45 B | 50 A 45 B |
| Conversion temperatures | K 6–12 N 71 is | K −2.5 to .6 N 68.5 is | K 9 to 14 N 69 is | K 17 to 20 N 74 is |
| $U_o$/V | — | 4.4 | 5.2 | |
| $t_E$ 50%/ms | — | 147 | 199 | |
| $t_A$ 50%/nm | — | 55 | 65 | |
| | | −1.2 | +0.76 | |

The measured values $\Delta\epsilon$, $U_o$, $t_E$ and $t_A$ refer to 20° C. $t_E$ 50% and $t_A$ 50% = starting or declining time at a change of the transmissibility of 50%, layer thickness 20 μm.

K = crystalline-solid
N = nematic
is = isotropic-liquid

As can be seen, already the addition of 5 mol-% causes a change of the sign of the dielectric anisotropy of the original dielectrically negative substances. Despite their relatively high melting points, the compounds 4 have good solubility in nematic mixtures, because of the low melting enthalpies. Most of the new compounds are not liquid-crystalline in themselves, however, they adapt to a nematic mixture, without considerably disturbing the liquid-crystalline order.

TABLE 1

1-oxa-2,6,7-trioxa-1-phosphabicyclo[2.2.2]octane-4-carboxylic acid ester 4

$$O=P\begin{pmatrix}O\\O\\O\end{pmatrix}\!\!-\!\!COO\!-\!R$$

| Compound | R | F.P. (°C.) | Melting enthalpy kJ/mol | IR(KBr) (1) P=O$^{(cm^{-1})}$ | $^1$H—NMR(CDCl$_3$) OCH$_2$C$^{(ppm)}$ |
|---|---|---|---|---|---|
| 3 | H | 260 (decomposes) | | 1285 | 5.10$^{(2)}$ |
| 4a | 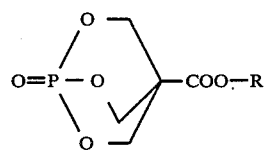 | 248–249 | | | 4.92; 5.30$^{(2)}$ |

TABLE 1-continued 1-oxa-2,6,7-trioxa-1-phosphabicyclo[2.2.2]octane-4-carboxylic acid ester 4

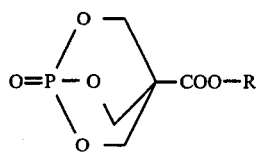

| Compound | R | F.P. (°C.) | Melting enthalpy kJ/mol | IR(KBr) (1) P=O$^{(cm-1)}$ | $^1$H—NMR(CDCl$_3$) OCH$_2$C$^{(ppm)}$ |
|---|---|---|---|---|---|
| 4b | —⟨○⟩—OC$_7$H$_{15}$ | 109 | 28 | 34  1330 | 4.90 |
| 4c | —⟨○⟩—OC$_8$H$_{17}$ | 81$^{(3)}$/107 | 21$^{(3)}$/22 | 38 | |
| 4d | —⟨○⟩—COO—⟨○⟩—OC$_4$H$_9$ | 206 | | 1335 | 4.93 |
| 4e | —⟨○⟩—CH(O—CH$_2$)$_2$—C$_6$H$_{13}$ | 187 | 21 | 1305 | 4.81 |
| 4f | —⟨○⟩—⟨○⟩—C$_6$H$_{13}$ | 193 | | | 5.06 |
| 4g | —⟨○⟩—(pyrimidine)—C$_6$H$_{13}$ | 200 (decomposes) | | | 5.08 |
| 4h | —⟨○⟩—CH(O—CH$_2$)$_2$—⟨○⟩—OC$_5$H$_{11}$ | 226$^{(4)}$ | | | 4.87 |

$^{(1)}$Values extrapolated from mixtures
$^{(2)}$absorbed in DMSO—D$_6$
$^{(3)}$Values for a metastable solid modification
$^{(4)}$K 226 N 230 T (decomposes)

We claim:
1. A nematic liquid crystal mixture including an added component for strongly increasing dielectric anisotropy and decreasing operating voltage, said added component comprising at least one 1-oxa-2-6,7-trioxa-1-phospha-bicyclo[2.2.2]octane-derivative having the general formula

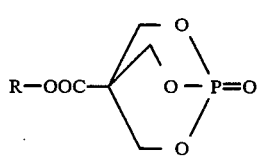

wherein $$R = R^1-\langle\bigcirc\rangle-, \quad R^2-CH(O-CH_2)_2-\langle\bigcirc\rangle-,$$

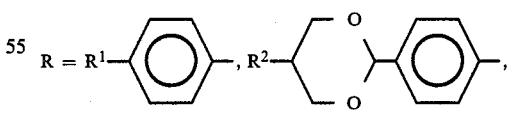

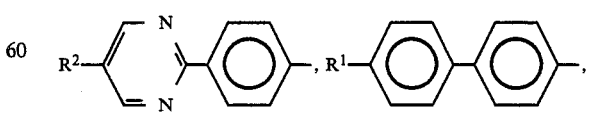

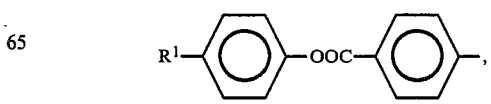

-continued

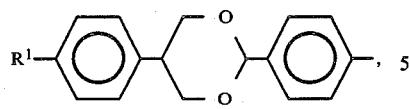

with $R^1 = C_nH_{2n+1}-$, $C_nH_{2n+1}O-$, $C_nH_{2n+1}COO-$, $C_nH_{2n+1}OCOO-$ $R_2 = C_nH_{2n+1}-$, with n=an integer from 1 to 10.

2. The nematic liquid crystal mixture of claim 1, in which, in the formula I, R is

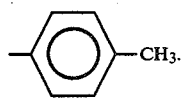

3. The nematic liquid crystal mixture of claim 1, in which, in the formula I, R is

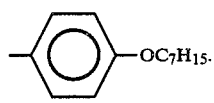

4. The nematic liquid crystal mixture of claim 1, in which, in the formula I, R is

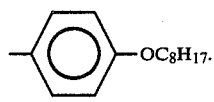

5. The nematic liquid crystal mixture of claim 1, in which, in the formula I, R is

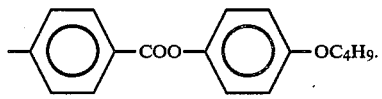

6. The nematic liquid crystal mixture of claim 11, in which, in the formula I, R is

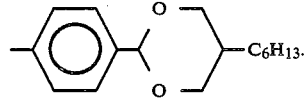

7. The nematic liquid crystal mixture of claim 1, in which, in the formula I, R is

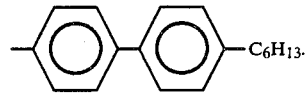

8. The nematic liquid crystal mixture of claim 1, in which, in the formula I, R is

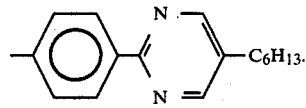

9. The nematic liquid crystal mixture of claim 1, in which, in the formula I, R is

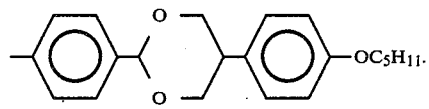

10. An optoelectronic display for the modulation of numbers, symbols, and images, the optoelectronic display containing a nematic liquid crystal mixture, the mixture being the mixture of claim 1.

11. 1-oxa-2,6,7-trioxa-1-phospha-bicyclo[2.2.2]octane-derivatives having the general formula

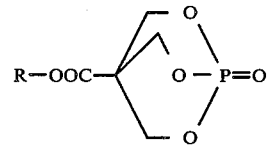

wherein $R = $ 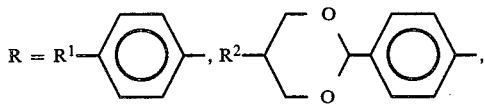

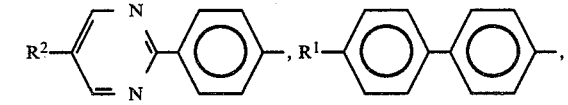

with $R^1 = C_nH_{2n+1}-$, $C_nH_{2n+1}O-$, $C_nH_{2n+1}COO-$, $C_nH_{2n+1}OCOO-$ $R^2 = C_nH_{2n+1}-$, with n=an integer from 1 to 10.

* * * * *